United States Patent [19]

Jones

[11] 4,418,581
[45] Dec. 6, 1983

[54] APPARATUS AND METHOD FOR SAMPLING A LIQUID

[76] Inventor: Richard W. Jones, 4 Upland Park Rd., Oxford, England, OX2 7RW

[21] Appl. No.: 262,904

[22] Filed: May 12, 1981

[30] Foreign Application Priority Data

May 13, 1980 [GB] United Kingdom ............... 8015727

[51] Int. Cl.³ ............................................. G01N 1/14
[52] U.S. Cl. ................................................ 73/864.34
[58] Field of Search ........... 73/863.83, 863.84, 864.34, 73/864.35

[56] References Cited

U.S. PATENT DOCUMENTS 3,949,611  4/1976  Watt .................................. 73/864.35
3,985,028  10/1976  Yoshida ............................ 73/864.34

*Primary Examiner*—S. Clement Swisher
*Attorney, Agent, or Firm*—Brisebois & Kruger

[57] ABSTRACT

An apparatus for sampling liquids flowing in open channels includes a cylinder into which liquid is drawn by the action of a large piston. When the piston is drawn to the top of the cylinder, liquid enters at the bottom of the cylinder by way of an inlet leading to a sample tube, the lower end of which is immersed in the channel. A small retaining tank is located at the base of the cylinder so that, when the piston is reversed and the liquid expelled from the cylinder, a small portion is retained in this tank. The tank leads to a sample valve which releases the contents of the tank into a collecting vessel at the end of each sampling cycle. A preferred embodiment of this invention has a vent valve to introduce pressurized air into the cylinder to purge liquid from the sampler. This apparatus is well suited for the application of pneumatic components to provide the control and the working power.

9 Claims, 1 Drawing Figure

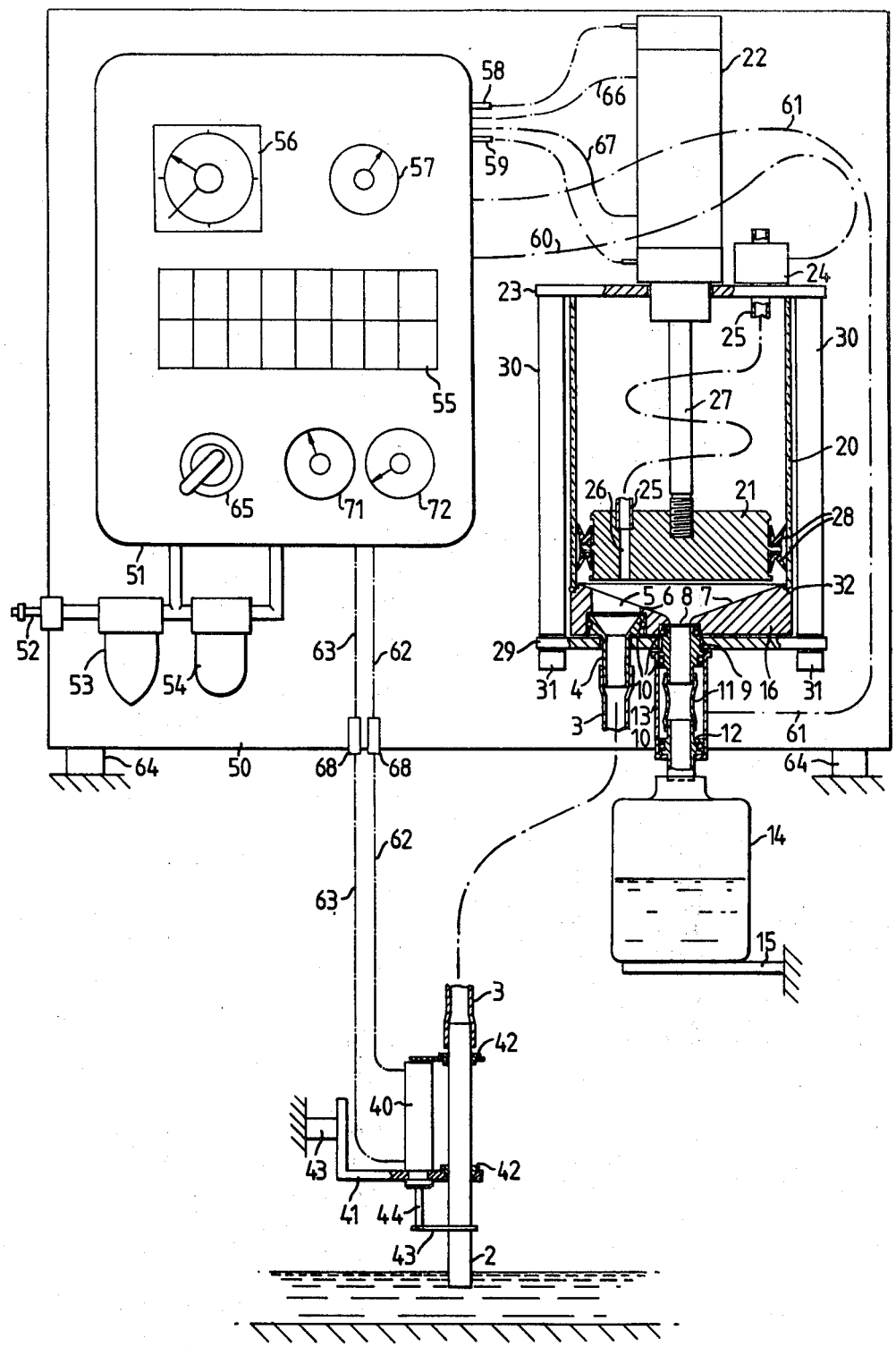

APPARATUS AND METHOD FOR SAMPLING A LIQUID

BACKGROUND OF THE INVENTION

The invention relates to apparatus and a method for periodically sampling a liquid and particularly to sampling wastewaters.

The purpose of sampling a liquid is to obtain a representative portion of the liquid from which its average composition can be determined. When sampling a flowing liquid, its average composition over a specific period of time is ofton required (for example, a 24 hour average). This is normally done by compositing a set of individual sub-samples taken with sufficient frequency to include all the effects of changes in composition of the flow during the period of the sample. The more frequent the taking of these individual samples, the more representative will be the composite sample.

The frequency of the sampling may be at regular time intervals or at time intervals in inverse proportion to the rate of flow of the sampled liquid. The latter case being referred to as flow-proportional sampling.

The individual sub-samples may be composited in a single container to give a gross average or alternatively, may be distributed into an array of separate containers to aportion the flow from hour to hour.

When sampling wastewaters it is important to include any solids waste that are being carried by the water. Wastewaters normally flow along open channels or ventilated drains and samples of this liquid are usually obtained by pumping a small volume into one or more containers at predetermined time intervals. Wastewaters often contain settleable particulate matter like washings and grit and also contain fine solids matter in suspension within the liquid. To obtain a representative sample of these solids, the wastewater must be pumped at high velocity to prevent the settleable matter from being left behind, and be transported through tubing of sufficient bore to avoid the risk of internal blockage within the sampling apparatus.

Wastewaters may also contain debris, rags and other large material aggregates which are not normally required to be included in the sample. These solids must not be allowed to accumulate at the inlet or where they may form an obstruction within the apparatus.

OBJECT OF THE INVENTION

It is an object of this invention to provide a means of obtaining liquid and wastewater samples in small volumes from a liquid periodically flowing at high velocity through tubing of large bore with apparatus that can easily be adapted to avoid obstruction by any debris flowing with the wastewater.

Other objects of this invention will be apparent hereinafter from the specification and from the recital of the appended claims, particularly when read in conjunction with the accompanying drawing.

SUMMARY OF THE INVENTION

According to the present invention, there is provided apparatus for and a method of sampling a liquid. The apparatus for sampling a liquid comprising:
(a) a working chamber;
(b) a vent valve for supplying compressed air to the working chamber;
(c) a bulk material inlet to the working chamber;
(d) a piston and cylinder combination whereby the pressure in the working chamber can be varied over a range from sub- to super-atmospheric;
(e) a drive means for reciprocating the piston;
(f) a catch tank;
(g) a lip for the catch tank disposed so that when material for sampling rises in the working chamber above the lip level, material flows into the tank and thereafter, when the material level falls below lip level, a given volume of material is retained in the tank;
(h) a sample outlet from the catch tank;
(i) a sample valve to control the flow of material along the sample outlet;
(j) a controller for regulating operation of the vent valve, the drive means and the sample valve.

The method of sampling a liquid comprising the steps of:
(i) closing the sample valve and opening the vent valve to admit compressed air into the chamber to be discharged through the bulk sample inlet thereby purging a duct connecting the inlet to a source of material to be sampled;
(ii) causing the drive means to operate the piston so that material from the source thereof is drawn into the working chamber by way of the inlet;
(iii) opening the vent valve and causing material in the working chamber to be driven therefrom by the compressed air pressure except in the case of material retained in the catch tank by means of the lip;
(vi) closing the vent valve, opening the sample valve and causing the drive means to operate the piston so that material retained in the catch tank at the end of the previous operation is driven out to a collector by way of the sample outlet.

A BRIEF DESCRIPTION OF THE DRAWING

FIG. 1. is an elevational view, partly broken away and sectioned, made in accordance with an embodiment of this invention.

DESCRIPTION OF THE PREFERRED EMBODIMENT

FIG. 1. shows an apparatus constructed in accordance with this invention and incorporating a working chamber that forms part of the cylinder. The apparatus includes a sampler housing 50 mounted on supports 64 and containing a controller 51 fed by air at a pressure of 60 to 120 p.s.i. through an air line 52 and thorugh an air filter 53 and air lubricator 54. The controller case incorporates an array of pneumatic logic units 55 of the Crouzet type (typically, AND, NOT, OR, and memory units). An air driven timer (typically Kuhnke 54.024) 56 is used to preset the required interval between samples, and variable delay timers 57, 71 and 72 are also part of the controller. A flexible inlet duct 3 of 16 mm bore leads from the housing 50 to an inlet pipe 2 which is supported by a lifting assembly. This lifting assembly comprises an inlet actuator 40 mounted on a bracket 41 and held by a support 43. The inlet actuator 40 is able to raise or lower the inlet pipe 2 in a vertical direction by moving the pipe/actuator link 43, the pipe 2 being guided by the slide bearings 42. The flexible duct 3 is joined to an inlet connector 4 within the sampler housing 50. This inlet connector leads to an inlet opening 5 in floor 7 of the working chamber formed by the base 16 and the glass cylinder 20. The opening 5 having a lip 6 below which a catch tank 8 is defined by profile of the floor 7. This profile is shaped to guide liquid towards the catch tank 8. Below the catch tank 8 an outlet connector 9 leads to a pinch valve assembly. The pinch valve assembly comprising an elastic tube 11 which is joined at its lower end to a delivery connector 12. The outlet and delivery connector together with the elastic tube 11 are housed within a valve case 13. Various rubber 'O' ring seals 10 are incorporated in the apparatus to prevent leakage of air or liquid. A collecting vessel 14 is held beneath the delivery connector 12 by a support 15. The working chamber base 16 supports the glass cylinder 20 of 150 mm bore on a vacuum sealing ring 32. The top of this cylinder is open and across this opening is mounted the actuator bridge 23 to which is fixed the air actuator 22. This air actuator, of 63 mm bore, and 160 mm stroke, is connected to the polypropylene piston 21 by an actuating rod 27. The gap between the piston 21 and the internal wall of the cylinder 20 is closed by a pair of rubber distributor seals 28. An air piloted, spring return vent valve 24 is also mounted on the actuator bridge 23, the vent valve being connected to an opening 26 through the piston 21 by a flexible nylon coiled tube 25. The working chamber assembly is held together by two alumunium side struts 30 which join the actuator bridge 23 to a lower platform 29 which supports the base 16. This assembly can be dismantled for cleaning by removing the two retaining screws 31. The controller 51 operates the air actuator 22 by air supply lines 58 and 59 and receives end-of-stroke signals from the actuator through the air lines 66 and 67. The pinch valve case 13 and the vent valve 24 are supplied by the controlling air lines 61 and 60 respectively. The inlet actuator 40 is operated by air pressure through lines 62 and 63 which pass through bulkhead connectors 68 in the housing 50. All these air supply lines are flexible nylon tubes.

In operation, sample interval timer 56 is preset to the required interval and the delay timers 57, 71 and 72 are set for typically 6 to 10 second delays. When the on/off switch 65 is switched on the interval timer 56 starts running but the sampling cycle does not commence until the preset interval has elapsed. During this period, the actuating cylinder 22, with the actuating rod 27 extended, holds the piston 21 at the bottom of the working chamber. The vent valve 24 is also closed, the pinch valve elastic tube 11 is open, and the inlet actuator 40 is retracted. When the time set on the interval timer 56 has elapsed the sampling cycle commences, and the following sequence occurs.

1. A pilot signal is sent through line 60 to open valve 24 and admit compressed air into the working chamber to purge flexible duct 3 and pipe 2. Simultaneously, the pressure in line 62 is raised and the pressure in line 63 released to cause the actuator 40 to lower the inlet tube 20 into the body of the liquid 1 and the delay timer 51 is set;
2. On expiration of the delay interval of timer 57, the controller 51 releases the signal in line 60 to close the vent valve 24, pressurises line 61 to close the elastic tube 11, releases the pressure in line 58 and raises the pressure in line 59 to cause the piston 21 to move towards the top of the cylinder 20 thereby creating sub-atmospheric conditions within the working chamber and causing liquid to be drawn from the main body 1 through the inlet tube 2 and duct 3 to the working chamber;
3. On receiving an end-of-stroke signal through line 66, the controller sets the delay timer 71 to allow liquid to continue to flow into the working chamber until equilibrium has been reached;
4. On expiration of the delay interval of timer 71, delay timer 72 is set and a pilot signal is sent through line 60 to open valve 24 to purge liquid from the working chamber back out through the inlet opening 5 but retaining a fixed volume within the catch tank 8;
5. On expiration of the delay interval of timer 72, the controller 51 continues the cycle by closing the vent valve 24, opening the elastic tube 11 by releasing the pressure on line 61, reversing the pressures in lines 62 and 63 to cause the inlet 2 to be raised by actuator 40 clear of the liquid surface and by reversing the pressures on lines 58 and 59 to cause the actuator 22 to move the piston 21 towards the bottom of the cylinder 20 thereby causing the air within the working chamber to purge any remaining liquid from the inlet pipe 2 and to drive the sample through the elastic tube 11 and the delivery connector 12 into the collecting vessel 14.

The apparatus has now returned to its initial state. This series of operations is then repeated at intervals set by the timer 56 to produce over a period of time a composite sample within the collecting vessel 14.

The above description of the preferred embodiment of the invention is exemplary, and the modifications to and variations of the specific embodiments could be made within the true scope of the invention which is be defined by the appended claims.

I claim:
1. A sampler for a substantially liquid material comprising:
   (a) a working chamber;
   (b) a vent valve for supplying compressed air to the working chamber;
   (c) a bulk material inlet to the working chamber;
   (d) a primary piston and cylinder combination whereby the pressure in the working chamber can be varied over a range from sub- to super-atmospheric;
   (e) a drive means for reciprocating the primary piston;
   (f) a catch tank;
   (g) a lip for the catch tank disposed so that when material for sampling rises in the working chamber above the lip level, material flows into the tank and thereafter when the material level falls below lip level, a given volume of material is retained in the tank;
   (h) a sample outlet from the catch tank;
   (i) a sample valve to control the flow of material along the sample outlet; and
   (j) a controller for regulating operation of the vent valve, the drive means and the sample valve.
2. A sampler as claimed in claim 1 wherein the working chamber forms a part of the cylinder.
3. A sampler as claimed in claim 1 or claim 2 wherein the drive means comprises a double action piston and cylinder combination with a connecting member couple the double action pistons to the primary piston.
4. A sampler as claimed in claim 2 wherein the walls of the cylinder are made at least in part of a transparent material to enable light-sensitive instruments to assess light transmitting characteristics of a sample in the cylinder.
5. A sampler as claimed in claim 1 wherein the vent valve is enabled to act on the working chamber by way of a passage in the piston adapted to vary the pressure in the working chamber.

6. A sampler as claimed in claim 1 wherein the controller, valves and drive means are adapted for operation from a supply of compressed gas.

7. A sampler as claimed in claim 1 wherein the bulk material inlet to the working chamber comprises a flexible duct whose end remote from the working chamber is displaceable by an auxiliary piston and cylinder combination whereby the remote end of the duct can be moved above and below a free surface of the material to be sampled.

8. A method of operating a sampler for a substantially liquid material of the type comprising, a working chamber, a vent valve for supplying compressed air to the working chamber, a bulk material inlet to the working chamber, a primary piston and cylinder for varying the pressure in the working chamber over a range from sub- to super-atmospheric, drive means for reciprocating the primary piston, a catch tank having a lip so disposed that when material for sampling rises in the working chamber above the lip level, material flows into the tank and when the material level falls below lip level, a given volume of material is retained in the tank, a sample outlet from the catch tank, and a sample valve to control the flow of material along the sample outlet, said method comprising, starting with the vent valve closed and the sample valve open, the following steps:
 (a) closing the sample valve and opening the vent valve to admit compressed air into the chamber for discharge through the bulk material inlet to purge a duct connecting the inlet to a source of material to be sampled;
 (b) causing the drive means to operate the primary piston to draw material from the source into the working chamber by way of the inlet;
 (c) opening the vent valve to admit compressed air to the working chamber to drive material from the working chamber except the material retained in the catch tank by means of the lip;
 (d) closing the vent valve, opening the sample valve, and causing the drive means to operate the piston to drive material retained in the catch tank out to a collector by way of the sample outlet.

9. A method according to claim 8 further comprising between steps (a) and (b), causing an auxiliary piston and cylinder combination to the remote end of the duct beneath a free surface of the material to be sampled; and between the steps (c) and (d), causing the auxiliary piston and cylinder combination to raise the remote end of the duct above the free surface of the material to be sampled.

* * * * *